US011793850B2

(12) United States Patent
Gao et al.

(10) Patent No.: US 11,793,850 B2
(45) Date of Patent: Oct. 24, 2023

(54) PLANT-DERIVED EXOSOME AS WELL AS PREPARATION METHOD AND APPLICATION THEREOF

(71) Applicants: Zhejiang University, Zhejiang (CN); Jiangsu Nanfang Medical Co., Ltd., Jiangsu (CN)

(72) Inventors: Jianqing Gao, Zhejiang (CN); Liming Li, Zhejiang (CN); Jiachen Chen, Zhejiang (CN); Ping Li, Jiangsu (CN)

(73) Assignees: Zhejiang University, Hangzhou (CN); Jiangsu Nanfang Medical Co., Ltd., Changzhou (CN)

( * ) Notice: Subject to any disclaimer, the term of this patent is extended or adjusted under 35 U.S.C. 154(b) by 153 days.

(21) Appl. No.: 17/148,808

(22) Filed: Jan. 14, 2021

(65) Prior Publication Data

US 2021/0213089 A1 Jul. 15, 2021

(30) Foreign Application Priority Data

Jan. 14, 2020 (CN) ......................... 202010037118.7

(51) Int. Cl.
*A61K 36/489* (2006.01)
*A61L 27/36* (2006.01)

(52) U.S. Cl.
CPC ........ *A61K 36/489* (2013.01); *A61L 27/3637* (2013.01); *A61L 27/3675* (2013.01); *A61K 2236/333* (2013.01); *A61K 2236/53* (2013.01); *A61L 2300/30* (2013.01); *A61L 2430/32* (2013.01)

(58) Field of Classification Search
None
See application file for complete search history.

(56) References Cited

FOREIGN PATENT DOCUMENTS

CN 103479682 A 1/2014

OTHER PUBLICATIONS

Rutter, B.D., et al., Isolation and Quantification of Plant Extracellular Vesicles, bio-protocol, vol. 7 1-13 (Sep. 5, 2017) DOI:10.21769/BioProtoc.2533 (Year: 2017).*

Rutter, B.D. & Innes, R.W., Extracellular Vesicles Isolated from the Leaf Apoplast Carry Stress-Response Proteins, Plant Physiology, Jan. 2017, vol. 173 (Year: 2017).*

Jeppesen, D.K., et al., Comparative analysis of discrete exosome fractions obtained by differential centrifugation, Journal of Extracellular Vesicles, 3:1, DOI: 10.3402/jev.v3.25011 (2014) (Year: 2014).*

Regente, M., et al., Vesicular fractions of sunflower apoplastic fluids are associated with potential exosome marker proteins, FEBS Letters 583 (2009)3363-66; Jan. 14, 2021 IDS (Year: 2009).*

Extracellular Vesicles Isolated from the Leaf Apoplast Carry Stress-Response Proteins; Brian D. Rutter and Roger W. Innes; Plant Physiology, Jan. 2017, vol. 173, pp. 728-741.

Vesicular fractions of sunflower apoplastic fluids are associated with potential exosome marker proteins; Mariana Regente, Georgina Corti-Monzón, Ana María Maldonado, Marcela Pinedo,Jesús Jorrín, Laura de la Canal; FEBS Letters 583 (2009) 3363-3366.

Exosome-like Nanovesicles Isolated from Citrus limon L. Exert Anti-oxidative Effect; Nicola Baldini,Elena Torreggiani,Laura Roncuzzi,Francesca Perut,Nicoletta Zini,and Sofia Avnet; Current Pharmaceutical Biotechnology, 2018, vol. 19, No. 11.

Plant extracellular vesicles; Yong Cui, Jiayang Gao, Yilin He & Liwen Jiang; Protoplasma vol. 257, pp. 3-12(2020).

Optimized Isolation of Extracellular Vesicles From Various Organic Sources Using Aqueous Two-Phase System; OK Kirba, BT Bozkurt, F Sahin, H Lmez, PN Tal Scientific Reports,(2019) 9:19159.

* cited by examiner

*Primary Examiner* — H. Sarah Park

(57) ABSTRACT

Disclosed a plant-derived exosome as well as a preparation method and an application thereof in preparation of drugs or scaffolds for animal tissue regeneration therapy. The preparation method includes: soaking and infiltrating any part of a natural plant with a 2-(N-morpholine) ethanesulfonic acid buffer solution; removing a supernatant; collecting a wet treated sample; refrigerating, centrifuging and extracting the sample to obtain apoplastic fluid, wherein the soaking and infiltrating method is as follows: vacuum supply is performed within 6-24 h after soaking for 2-5 times, vacuum supply time is independently 5-15 s each time, and interval time between two adjacent times of vacuum supply is independently 10 s-1 min; and centrifuging the apoplastic fluid at an ultra-high speed to obtain the plant-derived exosome, wherein ultra-high speed centrifugation conditions are as follows: centrifugal force is not lower than 100000 g, centrifugation time is 1-7 h, and a temperature is 0-4° C.

3 Claims, 2 Drawing Sheets

PLANT-DERIVED EXOSOME AS WELL AS PREPARATION METHOD AND APPLICATION THEREOF

CROSS-REFERENCE TO RELATED APPLICATIONS

This application claims the benefit of priority from Chinese Patent Application No. 202010037118.7, filed on Jan. 14, 2020. The content of the aforementioned application, including any intervening amendments thereto, is incorporated herein by reference in its entirety.

TECHNICAL FIELD

The present invention relates to the technical field of bioengineering, and particularly relates to a plant-derived exosome as well as a preparation method and an application thereof.

BACKGROUND OF THE PRESENT INVENTION

Tissue injuries including nerve tissue injury, bone injury and skin injury are a category of diseases that extensively threaten human health. One of the most major factors blocking tissue regeneration is an inhibitory microenvironment. Occurrence of acute trauma is accompanied with ischemia and edema; sharp oxidative stress response occurs in local injury; and excessive reactive oxygen species (ROS) is produced, thereby further causing secondary injury to tissues. Therefore, regulation of a local peroxidation microenvironment of the injury is an important way of tissue regeneration therapy.

Multiple plants are proved to have oxidation resistance. Plant-derived natural antioxidants such as rutin, anthocyanin and curcumin have been applied to antioxidant researches and tissue regeneration researches. However, these products have different properties, and often have the following problems: solubility is low; extraction and purification processes are complex; effective bio-utilization depends on corresponding preparation delivery, and the like. In addition, antioxidant ingredients in the plants not only are limited to compound molecules, but also include RNA and other components. Therefore, based on the antioxidant active ingredients of the natural plants, developing an efficient and safe compound therapeutic formulation with general applicability has excellent clinical application value.

Exosome is of a vesicle structure produced by cells, includes proteins, mRNA and miRNA, and has important functions such as intercellular communication and material transportation. The exosome has a small particle size of 40-150 nm, is of a lipid structure similar to cytomembrane, and easily passes through various barriers of the body. Moreover, a phospholipid bilayer structure enables the exosome to have low immunogenicity, and can conduct long circulation in organisms. Through the above characteristics, it is widely concerned that the exosome becomes a natural therapeutic. Studies have shown that, exosomes in *arabidopsis* leaves contain multiple antioxidant ingredients. However, there are no related applications and researches on extraction and tissue engineering therapy of plant exosomes at present.

To sum up, establishment and application of the preparation method of plant-derived exosomes have significances and prospects in tissue regeneration therapy.

SUMMARY OF THE PRESENT INVENTION

With respect to defects in the art, the present invention provides a preparation method of a plant-derived exosome. The method is simple and easy to manipulate, is applicable to fresh plants and other plant samples dried and preserved in different manners, and does not need any other purification step. Thus, the plant-derived exosome that can directly serve as a therapeutic formulation can be prepared through direct treatment of the plants only.

A preparation method of the plant-derived exosome includes the following steps:

(1) soaking and infiltrating any part of a natural plant with a 2-(N-morpholine) ethanesulfonic acid buffer solution; removing the supernatant; collecting a wet treated sample; refrigerating, centrifuging and extracting the sample to obtain apoplastic fluid;

wherein soaking and infiltrating method is as follows: vacuum supply is performed within 6-24 h after soaking for 2-5 times, vacuum supply time is independently 5-15 s each time, and interval time between two adjacent times of vacuum supply is independently 10 s-1 min; and (2) centrifuging the apoplastic fluid at an ultra-high speed to obtain the plant-derived exosome, wherein ultra-high speed centrifugation conditions are as follows: centrifugal force is not lower than 100000 g, centrifugation time is 1-7 h, and a temperature is 0-4° C.

In the present invention, the plant is soaked in the buffer solution and then centrifuged so as to extract the apoplastic fluid. Since bound water in apoplast of the plant is not lost along the drying process, the method is applicable to fresh plants and also applicable to dry plants that have been dried or aired. The extracted plant-derived exosome is clear in outline and integral in structure.

During soaking treatment with the buffer solution, the buffer solution cannot fully immerse the apoplast of the plant if soaking time is insufficient; and if the soaking time is too long, partial active ingredients may deteriorate. Preferably, the soaking time is 12-18 h.

In the preparation method of the present invention, vacuum supply is performed on a buffer solution system soaked with plants. Thus, gases in the plants may be extracted under a negative pressure, so that the buffer solution fully penetrates into the plants. In case of single vacuum treatment or too short time, the buffer solution cannot fully penetrate into the plant; in case of frequent vacuum treatment or too long time, the plant or exosome thereof may be damaged, subsequent extraction is affected by excessive residues, or the exosome structure is damaged; if interval time of vacuum supply is too long each time, extraction efficiency is lowered; and if interval time is too short, an ideal effect cannot be achieved. Preferably, vacuum supply conditions are as follows: vacuum supply time is 10 s each time; interval time is 30 s each time; and vacuum supply is conducted for totally 3 times.

The 2-(N-morpholine) ethanesulfonic acid buffer solution includes the following raw materials: 2-(N-morpholine) ethanesulfonic acid, NaCl, $CaCl_2 \cdot H_2O$ and water.

Preferably, a pH value of the 2-(N-morpholine) ethanesulfonic acid buffer solution is regulated to 5.5-6.5 with NaOH.

Preferably, in the step (1), refrigerating and centrifuging conditions are as follows: the centrifugal force is 600-800 g; the centrifugation time is 15-25 min. In case of extremely high centrifugal force or too long centrifugation time, excessive residues are produced; and in case of extremely low centrifugal force or too short centrifugation time, the apoplast cannot be fully extracted.

Preferably, before ultra-high speed centrifugation of the apoplastic fluid, centrifugal fragment removal treatment is performed at a low temperature of 0-4° C., including the following steps:

(I) performing low-speed centrifugal treatment for 1-3 times, wherein conditions of each low-speed centrifugal treatment independently include a centrifugal force of 2500-3500 g and centrifugation time of 15 min-1 h; and (II) performing high-speed centrifugal treatment, wherein conditions include a centrifugal force of 9000-11000 g and centrifugation time of 15 min-1 h.

Gradient centrifugation is performed before ultra-high speed centrifugation, and thus extremely large plant residues and cell fragments may be fully removed. If centrifugal fragment removal is not performed or the centrifugal force is low or centrifugation is insufficient, lots of residues are accompanied in subsequent extraction, thereby lowering extraction purity of the exosome; and if the centrifugal force is extremely high during fragment removal or the frequency of centrifugation is too high or time is too long, the exosome may be easily lost, thereby lowering yield of the exosome. Further preferably, the low-temperature centrifugal fragment removal conditions are as follows: the centrifugal force is 3000 g, centrifugation is performed for 20 min, and centrifugation is totally performed for 2 times; and then centrifugation is performed once for 30 min at a centrifugal force of 10000 g, and a centrifugal temperature is 4° C.

The present invention further provides a plant-derived exosome prepared by the preparation method. The exosome is clear in outline and integral in structure, has a particle size of 50-150 nm, is of a cup-like vesicle structure, and can be applied to tissue regeneration therapy such as local treatment and tail vein injection treatment after tissue injury.

The present invention further provides an application of the plant-derived exosome in preparation of drugs or scaffolds for animal tissue regeneration therapy.

Preferably, the animal tissues are nerve tissues.

Compared with the prior art, the present invention has major advantages as follows:

(1) According to the method in the present invention, any other purification step is not needed; and the therapeutic formulation may be prepared by direct treatment of the plant only.

(2) The method in the present invention is applicable to fresh plants and other plant samples dried and preserved in different manners.

(3) The preparation method is simple and easy to control.

(4) An antioxidant effect of the prepared plant-derived exosome in nerve tissue regeneration is better than that of a single material and drug, which proves that the exosome has excellent application prospects and research values.

DETAILED DESCRIPTION OF THE PRESENT INVENTION

The present invention will be further described below in combination with drawings and specific embodiments. It should be understood that, these embodiments are merely used for describing the present invention, rather than limiting the scope of the present invention. Operating methods without specific indicated conditions in embodiments below are generally conducted in accordance with general conditions or conditions suggested by manufacturers.

1. A preparation method of a plant-derived exosome:

4.26 g of 2-(N-morpholine) ethanesulfonic acid, 5.85 g of NaCl and 0.27 g of $CaCl_2 \cdot H_2O$ were dissolved into ultrapure water; a pH value of the solution was regulated to 6.0 with 5M of NaOH solution; a 2-(N-morpholine) ethanesulfonic acid buffer solution was prepared.

Dried *Sophora japonica* was soaked in the above buffer solution for 12-18 h and subjected to vacuum supply for 10 s after soaking for preset time; interval time was 30 s each time; and vacuum supply was performed for totally 3 times.

The supernatant was removed; a wet treated *Sophora japonica* sample was collected and filled in an outer barrel of a syringe; the syringe barrel was placed in a 50 mL of centrifuge tube; and the sample was refrigerated, centrifuged and extracted so as to obtain apoplastic fluid, wherein a centrifugal force was 700 g, and centrifugation time was 20 min.

The obtained apoplastic fluid was collected and subjected to centrifugal treatment at 4° C. so as to remove fragments; centrifugation was performed twice at a centrifugal force of 3000 g for 20 min; then centrifugation was performed once at a centrifugal force of 10000 g for 30 min; and finally the supernatant was collected.

The supernatant was centrifuged at a centrifugal force of 100000 g for 3 h at a temperature of 4° C.; the supernatant was removed; and a precipitate was collected, thereby obtaining the plant-derived exosome.

Figure 1:
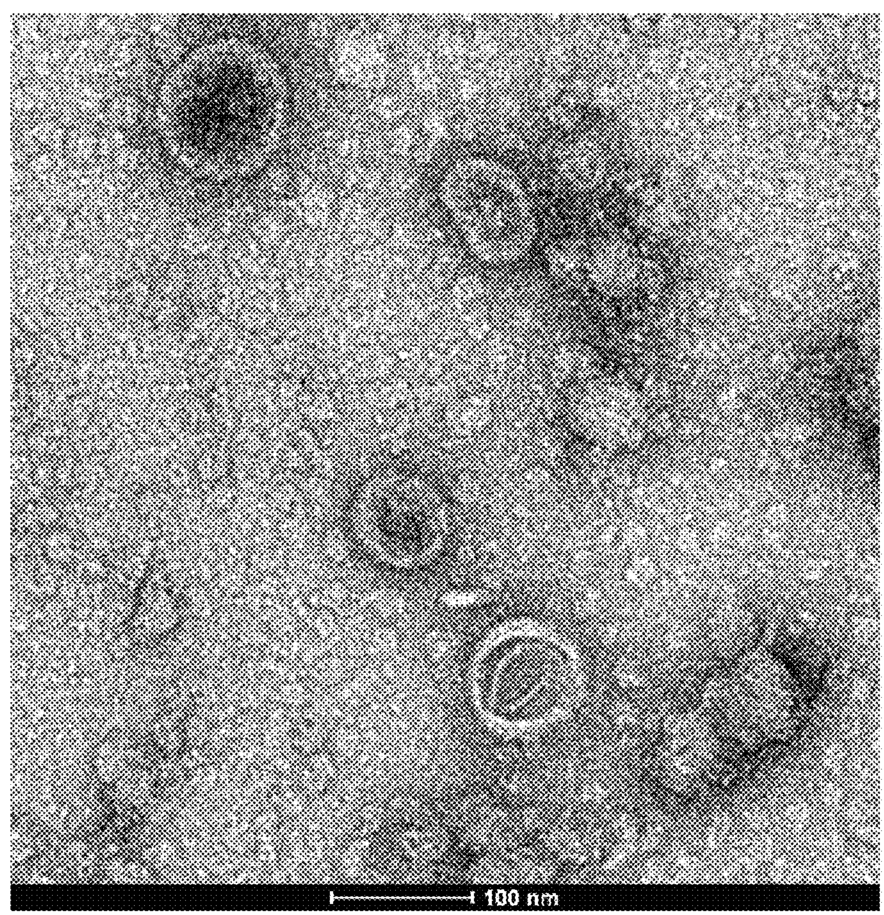
FIG. 1 is a transmission electron microscope morphology observation photo of a *Sophora japonica* exosome prepared in embodiments.

A transmission electron microscope photo of the extracted plant-derived exosome is shown in FIG. 1. It shows that, the prepared plant-derived exosome has a particle size of about 100 nm and is of a typical cup-like exosome vesicle structure.

Figure 2:
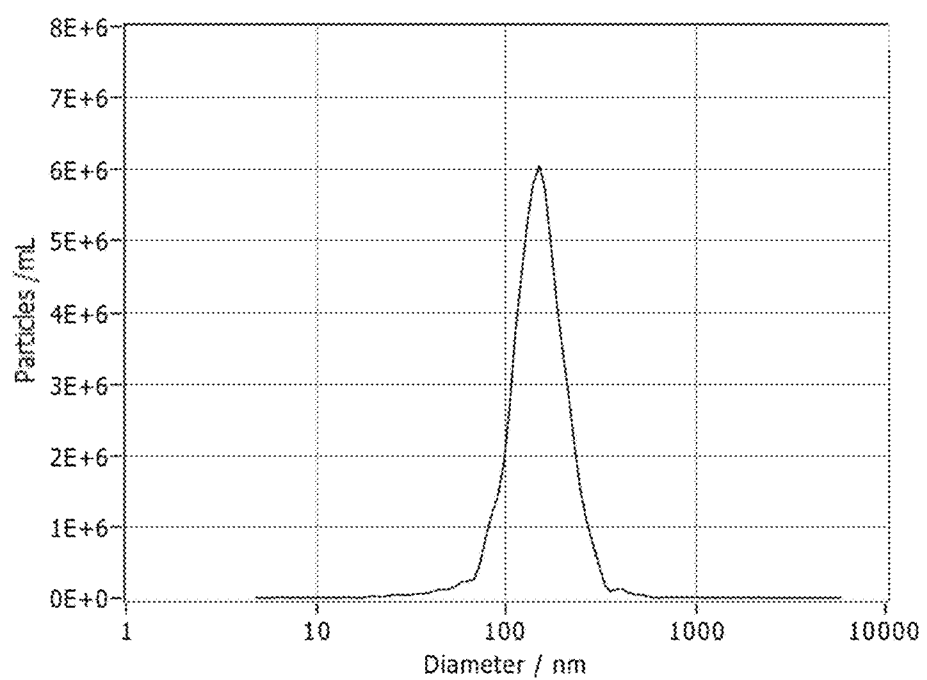
FIG. 2 is a particle size analysis result diagram of a *Sophora japonica* exosome prepared in embodiments by a particle tracking analyzer, wherein in the figure, a horizontal coordinate represents the particle size, and a vertical coordinate represents a number of particles per ml.

A detection result of the extracted plant exosome by a particle tracking analyzer is shown in FIG. 2. It shows that, the prepared plant-derived exosome has a main particle size distribution of about 150 nm and is in line with the definition of the particle size of the exosome.

2. Preparation method of a dopamine enveloped hyaluronic acid (HA) hydrogel scaffold:

Aldehyde groups and amino were respectively grafted on molecular chains of HA; and Schiff base condensation was conducted, thereby obtaining the hydrogel scaffold.

500 mg of HA having a molecular weight of 2.3 MDa was weighed and dissolved into 150 mL of ultrapure water; 134 mg of $NaIO_4$ was weighed and dissolved into 13.4 mL of water; an aqueous solution of HA was added dropwise in dark conditions; the solution was stirred and reacted for 2 d; 600 μL of ethylene glycol was added; the solution was continuously stirred for 1 h; and the solution was freeze-dried within 3 d after dialysis so as to obtain aldehyde-modified HA.

270 mg of HA having a molecular weight of 1.3 MDa was dissolved into 150 mL of ultrapure water; 4.644 g of adipic acid dihydrazide (ADH) was added and uniformly stirred; 0.96 g of 1-(3-dimethyl aminopropyl)-3-ethyl carbodiimide hydrochloride and 0.675 g of 1-hydroxybenzotriazole were dissolved into 10 mL of a mixed solution of dimethyl sulfoxide and water according to a ratio of 1:1; the mixed solution was dropwise added into the HA solution; a pH value was maintained at 6.8; the solution was stirred for 4 h; and the reaction was terminated when the pH value was regulated to 7, and the solution was freeze-dried within 3 d after dialysis so as to obtain amino-modified HA.

The amino-modified HA was dissolved into a PBS buffer solution so as to prepare a 12 mg/mL of solution; the aldehyde-modified HA was dissolved into the PBS buffer solution so as to prepare a 20 mg/mL of solution; the 12 mg/mL of solution and the 20 mg/mL of solution were mixed in an isovolumetric manner and then stood so as to form gel.

The hydrogel was freeze-dried and then swelled in a Tris buffer solution having a pH of 8.5 so as to form a 1 mg/mL of dopamine Tris solution; the swelling hydrogel was stirred in the solution overnight in dark conditions, thereby obtaining the dopamine enveloped hydrogel.

3. Animal experiment:

(1) Establishment of spinal cord injury (SCI) injury:

Female SD rats having the weight of 220-250 g were selected and subjected to SCI model establishment surgery.

The rats were anesthetized with 1% of pentobarbital sodium; hair on the back of the anesthetized rats was shaved off; T9-T10 sections of the spines were found; by taking the T9-T10 sections as the center, upper and lower parts of the spines were cut open by 2 cm by an operating knife so as to expose the spinal backs; and muscles on two sides of the spines on the T9-T10 sections were isolated.

The spines with free muscular tissues were cut open so as to expose the spines; spinal cord tissues were clipped; fractures of about 4 mm were made; through inspection of microscope forceps, it was ensured that the spines were fully isolated; bleeding was stopped; residual tissues were wiped; the hydrogel was transplanted to the spinal injury fractures; 20 μL of PBS suspension (P-ES group) of the prepared *Sophora japonica* exosome was injected by a micropipettor; a hydrogel scaffold was transplanted after the spines were cut off in a blank group without injecting the exosome; and the wound was stitched and daubed with iodine tincture.

The rats were killed within 7 days after modeling; and spinal cord tissues of the rats were taken and subjected to immumohistochemical staining inspection with a peroxidation product, i.e., 4-hydroxynonenal (4-HNE).

Figure 3:
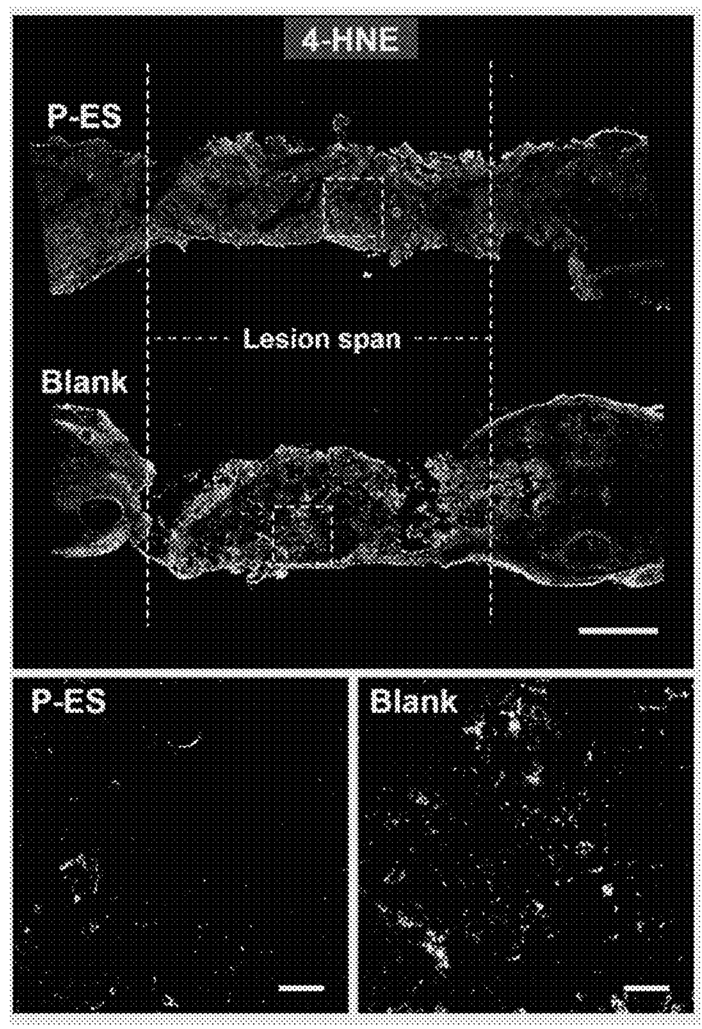
FIG. 3 is a staining result diagram of an intra-tissue peroxidation product of a *Sophora japonica* exosome prepared in embodiments in combination with biological scaffold material transplantation and scaffold material transplantation alone for treatment of spinal cord injury of rats, wherein in the figure, scale of the upper figure is 1 mm, and the scale of two lower figures is 100 μm.

Partial regions of a lesion span of P-ES group and blank group in a figure located on the upper part of FIG. 3 were respectively intercepted and magnified so as to obtain two smaller figures located on the lower part of FIG. 3. As shown in FIG. 3, antioxidation of the plant-derived exosome is relatively obvious. Through treatment of the plant-derived exosome, the amount of a peroxidation injury product, i.e., the 4-HNE, in the tissues is decreased significantly.

In addition, it should be understood that, after reading the above descriptions of the present invention, those skilled in the art may make various changes or modifications to the present invention. These equivalent forms shall be included in the scope defined by claims in the present application.

What is claimed is:

1. A method for preparing a *Sophora japonica*-derived exosome, comprising:

a) soaking a *Sophora japonica* sample with a 2-(N-morpholino)ethanesulfonic acid buffer solution, and performing vacuum supply 2-5 times with 5-15 seconds each time within 6-24 hours to produce a first supernatant, wherein the vacuum supply is performed every 10 seconds-1 minute;

b) removing the first supernatant obtained in step a) to collect a wet treated sample;

c) centrifuging the wet treated sample under a refrigerating condition to extract an apoplastic fluid from the wet treated sample;

d) performing centrifugal fragment removal treatment comprising: performing centrifugation on the apoplastic fluid obtained in step c) for 15 minutes-1 hour at a centrifugal force of 2500-3500 g and a centrifugation temperature of 0-4° C., followed by another centrifugation for 15 minutes-1 hour at a centrifugal force of 9000-11000 g and a centrifugation temperature of 0-4° C. to produce a second supernatant; and e) centrifuging the second supernatant obtained in step d) for 1-7 hours at a centrifugal force of not lower than 100000 g and a centrifugation temperature of 0-4° C. to obtain the *Sophora japonica*-derived exosome.

2. The method of claim 1, wherein the 2-(N-morpholino) ethanesulfonic acid buffer solution comprises 2-(N-morpholino)ethanesulfonic acid, NaCl, $CaCl_2 \cdot H_2O$ and water; and a pH of the 2-(N-morpholino)ethanesulfonic acid buffer solution is 5.5-6.5.

3. The method of claim 1, wherein in step c), a centrifugal force is 600-800 g; and a centrifugation time is 15-25 minutes.

* * * * *